(12) United States Patent
Manhart

(10) Patent No.: US 10,839,498 B2
(45) Date of Patent: Nov. 17, 2020

(54) METHOD AND APPARATUS FOR GENERATING A SET OF PROCESSED IMAGES

(71) Applicant: Siemens Healthcare GmbH, Erlangen (DE)

(72) Inventor: Michael Manhart, Fürth (DE)

(73) Assignee: Siemens Healthcare GmbH, Erlangen (DE)

(*) Notice: Subject to any disclaimer, the term of this patent is extended or adjusted under 35 U.S.C. 154(b) by 189 days.

(21) Appl. No.: 16/015,816

(22) Filed: Jun. 22, 2018

(65) Prior Publication Data
US 2018/0374204 A1 Dec. 27, 2018

(30) Foreign Application Priority Data
Jun. 22, 2017 (EP) .................................. 17177310

(51) Int. Cl.
| | | |
|---|---|---|
| *G06T 5/50* | (2006.01) | |
| *A61B 6/00* | (2006.01) | |
| *G06T 5/00* | (2006.01) | |
| *G06T 5/20* | (2006.01) | |
| *G06T 3/00* | (2006.01) | |
| *G06T 7/00* | (2017.01) | |
| *G06T 7/30* | (2017.01) | |

(52) U.S. Cl.
CPC ................ *G06T 5/50* (2013.01); *A61B 6/481* (2013.01); *A61B 6/5241* (2013.01); *G06T 3/0068* (2013.01); *G06T 5/002* (2013.01); *G06T 5/20* (2013.01); *G06T 7/0012* (2013.01); *A61B 6/504* (2013.01); *G06T 7/30* (2017.01); *G06T 2207/10116* (2013.01); *G06T 2207/20024* (2013.01); *G06T 2207/20224* (2013.01); *G06T 2207/30004* (2013.01)

(58) Field of Classification Search
USPC .................................................. 382/130–132
See application file for complete search history.

(56) References Cited

U.S. PATENT DOCUMENTS

| | | | | |
|---|---|---|---|---|
| 6,097,833 A | * | 8/2000 | Lobregt | A61B 6/481 348/E5.089 |
| 7,555,100 B2 | * | 6/2009 | Wang | A61B 6/02 378/98.12 |

(Continued)

FOREIGN PATENT DOCUMENTS

| | | |
|---|---|---|
| DE | 102008003945 B3 | 7/2009 |
| DE | 102015224806 A1 | 6/2017 |

OTHER PUBLICATIONS

European Search Report for European Patent Application No. 17177310.4-1666, dated Dec. 12, 2017.

*Primary Examiner* — Ishrat I Sherali
(74) *Attorney, Agent, or Firm* — Lempia Summerfield Katz LLC

(57) ABSTRACT

A method and an apparatus for generating a set of processed images of an object from overlapping raw images are provided. The raw images are aligned so that pixels representing a same part of the picture object in different raw images are aligned forming a respective pixel stack for each pictured part of the object. At least one mask image is then generated by a maximum intensity projection through the pixel stacks. The set of processed images is then generated from the raw images using the at least one mask image.

18 Claims, 3 Drawing Sheets

(56) References Cited

U.S. PATENT DOCUMENTS

| | | |
|---|---|---|
| 8,792,616 B2 | 7/2014 | Tanaka et al. |
| 9,918,688 B2 * | 3/2018 | Kyriakou .............. G06T 7/0016 |
| 2005/0127910 A1 | 6/2005 | Visser et al. |
| 2008/0152088 A1 | 6/2008 | Wang et al. |
| 2009/0180676 A1 | 7/2009 | Pfister et al. |
| 2011/0044524 A1 * | 2/2011 | Wang ..................... G01R 33/54 |
| | | 382/131 |
| 2012/0121147 A1 * | 5/2012 | Huang ..................... G06T 7/11 |
| | | 382/131 |
| 2015/0208996 A1 | 7/2015 | Kyriakou |
| 2016/0247325 A1 | 8/2016 | Yu et al. |
| 2017/0169553 A1 | 6/2017 | Manhart |

\* cited by examiner

METHOD AND APPARATUS FOR GENERATING A SET OF PROCESSED IMAGES

This application claims the benefit of EP 17177310.4, filed on Jun. 22, 2017, which is hereby incorporated by reference in its entirety.

BACKGROUND

The present embodiments relate to generating a set of processed images of an object from overlapping raw images. For example, the present embodiments may be used for a peripheral digital subtraction angiography.

DE 10 2008 003 945 B3 discloses a method for creating images relating to a system of blood vessels of a patient using digital subtraction angiography. Therein, multiple images are taken in different positions following a dispersal of a contrast agent through the system of blood vessels. From a first image, an image part the contrast agent has not yet spread is used as a mask for a spatially corresponding image part of a second image.

U.S. Pat. No. 8,792,616 B2 discloses an x-ray image diagnosis apparatus and an x-ray image processing method. Therein, an imaging unit may perform a step movement process such that images of a subject are taken at a plurality of stages. A plurality of regions of interest for a plurality of locations in both legs of the subject is set when an image is taken after a contrast medium is injected into a lower limb of the subject. A change of an image level in the regions of interest is then measured to detect a flow of the contrast medium The imaging unit and/or a top panel is then moved to a next imaging stage based on a change in the image level of a leg in which the contrast medium flows more slowly. Image data taken at the plurality of stages is then processed.

SUMMARY AND DESCRIPTION

The scope of the present invention is defined solely by the appended claims and is not affected to any degree by the statements within this summary.

The present embodiments may obviate one or more of the drawbacks or limitations in the related art. For example, improved processed images contrasted with a contrast agent, with improved flexibility and usability, are obtained.

A method according to one or more of the present embodiments is concerned with generating a set of processed images of an object from overlapping raw images. The raw images are obtained by a single contrast run. A contrast run refers to the process of injecting a contrast agent into the object and taking a series of raw images of the object using an imaging device to picture different stages of dispersal of the contrast agent in the object. The imaging device may, for example, be an x-ray apparatus. The images may therefore, for example, be x-ray images. After the raw images are obtained and provided for processing, the raw images are aligned so that pixels representing the same part of the pictured object in different raw images are aligned forming a respective pixel stack for each pictured part of the object. This provides that each pixel is correlated to all other pixels corresponding to (e.g., picturing or representing) the same part of the object. A part of the object in this sense is a detail or an element of the object that is captured in only a single pixel in each image picturing this specific part.

A pixel stack therefore includes all pixels of all raw images corresponding to a specific part of the object. This same part of the object may be pictured in multiple raw images because the raw images or corresponding contents at least partly overlap each other. Every raw image may have the same number of pixels, whereas the pixel stacks may have different numbers of pixels (e.g., the pixel stacks may have different heights).

Once the raw images are aligned, at least one mask image is generated by a maximum intensity projection (MIP) through the pixel stacks of the aligned raw images. This provides that for each pixel stack, the respective one pixel with the highest intensity value is determined. These maximum intensity values or pixels from all pixel stacks are then put together to create the at least one mask image. If only a single mask image is created or generated using the maximum intensity pixels from all pixel stacks, then this single mask image covers an entire area pictured or captured during the single contrast run. In this case, the single mask image may be larger than a single raw image. It is, however, also possible to generate multiple mask images, where each mask image may, for example, be the same size as the raw images and may, therefore, be smaller than the total area or region imaged in the single contrast run. In case multiple mask images are generated, a respective subset of the pixel stacks may be used for each of the multiple mask images.

The number of mask images may be equal to the number of raw images, and each mask image may correspond to one raw image, providing that a respective mask image may picture or cover the same area of the object as the corresponding raw image.

In a next act of the method according to one or more of the present embodiments, the set of processed images is generated from the raw images using the at least one mask image. This act may include subtracting the at least one mask image from the raw images. If only one mask image is generated, this same mask image may be subtracted from each raw image. For this purpose, the mask image and the respective raw image may be aligned so that each pixel of the raw image or the corresponding intensity value is subtracted from the corresponding pixel of the respective raw image or the corresponding intensity value. Corresponding pixels represent or picture the same part of the object. Since the mask image is assembled with pixel-level precision after the raw images have been aligned, all data needed for subtracting the at least one mask image from the raw images with pixel-level precision or accuracy is available. The same procedure may be used if more than one mask image is generated. If the number of mask images is equal to the number of raw images and each mask image pictures the same area as the respective corresponding raw image, subtracting the mask images from the corresponding raw images may be done with particularly little effort since the same coordinate system may be used for the mask images and the raw images; thus, no alignment or registration is necessary.

In terms of the present embodiments, a raw image may be image data captured and output by a detector of the imaging device. The detector may be or include an x-ray detector. The detector may include a multiplicity of pixels that may correspond to the pixels of the raw images. A raw image may, however, have been reconstructed or generated from raw image data output by the detector or the imaging device. Therefore, one or more image processing acts may be executed using a conventional image processing algorithm prior to the maximum intensity projection. Similarly, one or more image processing acts may be applied to the raw images in addition to using the at least one mask image to generate the set of processed images. Using the at least one mask image to generate the set of processed images may, for example, include subtracting the at least one mask image from the raw images.

The raw images show all parts of the object made visible by the respective imaging technique used to capture or generate the raw images. This may, for example, include bones as well as different kinds of soft tissue, organ tissue, and/or connective tissue in addition to the contrast agent in a respective stage of dispersal. Since only a respective maximum intensity value for each part of the object or the region captured during the single contrast run is used for the at least one mask image and the contrast agent lowers the detected intensity, the mask image does not show the contrast agent. This is at least the case for every part of the object or the imaged area that has been imaged at least once during the single contrast run or contrast acquisition without the contrast agent flowing through this particular part. By using the mask image (e.g., by combining the at least one mask image with the raw images), the contrast agent or the respective corresponding parts of the object flooded with the contrast agent may be emphasized and made visible more clearly in the processed images. At the same time, parts of the object not flooded with the contrast agent may be removed and are therefore not shown in the processed images. The proposed method may, in other words, be employed for techniques such as peripheral digital subtraction angiography.

Since the at least one mask image may be a compound image put together using parts of different raw images, there is no need for a separate mask run to obtain a mask image prior to injecting the contrast agent. This may allow employing imaging technique with lowered exposure of the object due to the omitted mask run. Another advantage of the present embodiments is that by omitting the mask run, overall less time is required for the imaging process, which again reduces strain on the object (e.g., a patient). Additionally, the resulting processed images may be improved, while at the same time, lowering the requirements that are to be met by the imaging device and respective operating personnel for a successful execution of the imaging procedure or process and the proposed method. This is the case, because only the single contrast run and no separate mask run is necessary, which eliminates the need for precise repositioning of the imaging device for two separate runs. Additionally, since it is not required to use fixed and predetermined parts of each raw image to generate the at least one mask image, it becomes possible to use raw images acquired in a continuous fashion, such as, for example, as a video feed. This may also eliminate the need for a respective operating personnel to manually advance the imaging device during the contrast run, which may be challenging and may require significant experience and expertise. The acquisition of the raw images as well as the generation of the processed images may therefore be fully automated.

The method of aligning the overlapping raw images with pixel-level precision and exploiting or using the resulting pixel stacks also enables the use of noise reducing image processing techniques to improve an image quality of the resulting processed images.

In a development of the present embodiments, at least one noise-reduced mask image is generated from the aligned raw images. This is done by discarding all pixels from the pixel stacks having intensity values lower than a predetermined threshold value. A weighted average of the intensity values of the remaining pixels of each pixel stack is then calculated to generate the at least one noise-reduced mask image. The at least one noise-reduced mask image is then subtracted from each corresponding raw image to generate the set of processed images.

The methods and possibilities as well as the corresponding advantages as described with reference to the at least one mask image may also be applied to the at least one noise-reduced mask image. This refers to generating the at least one mask image as well as to subtracting the at least one mask image from the raw images.

The predetermined threshold value may be chosen or provided in dependence of the used contrast agent and/or an expected intensity for pixels imaging parts of the object that are flooded with the contrast agent. The predetermined threshold value may therefore also depend on an imaging technique used to acquire the raw images and/or on a relative location or position of a region to be flooded with the contrast agent within the object. If, for example, this flooded region is located deep within the object and surrounded by dense material such as bone, the expected intensity and, therefore, the predetermined threshold value may be relatively lower. In case of a thinner object not containing any dense material, the expected intensity and, therefore, the predetermined threshold value may be relatively higher.

Discarding all pixels with intensity values below the predetermined threshold value may provide that parts of the raw images picturing or corresponding to parts of the object flooded with the contrast agent are not used to generate the noise-reduced mask image or images. The predetermined threshold value may, for example, be given as an absolute intensity value or as a relative intensity value with respect to a characteristic of the imaging device, such as an intensity output by a radiation source of the imaging device and/or a sensitivity of the detector of the imaging device.

Since the respective weighted average intensity is used for the pixels of the noise-reduced mask image, noise, detection errors, and/or measuring errors, for example, are averaged out or minimized, resulting in an improved image quality of the at least one noise-reduced mask image, and ultimately in an improved image quality of the processed images. In case the at least one noise-reduced mask image is generated, only this noise-reduced mask image and not the at least one mask image may be subtracted from the raw images to generate the set of processed images.

In a further development of the present embodiments, the at least one mask image is used as a reference for generating the at least one noise-reduced mask image. Since the at least one mask image features a maximum measured intensity for each of its pixels, the predetermined threshold value may be given as a relative value in relation to the corresponding intensity of the at least one mask image. This approach is advantageous since external factors such as the intensity output by a radiation source, or a characteristic of the detector, as well as a geometry of the imaged object do not have to be explicitly taken into account or considered in determining the threshold value.

For calculating the weighted average of all intensity values of the remaining pixels, a monotonous weight function may be provided and applied to the intensity values of the remaining pixels for each pixel stack. The weight function may be constant, providing that all intensity values in each respective pixel stack are weighted equally. This may result in optimal noise reduction. Alternatively, a non-constant weight function may be used. For example, a step function may be used as the weight function to combine this step with the above-mentioned thresholding. The step function may apply equal non-zero weights to all intensity values above the predetermined threshold value and a weight of zero to all intensity values equal to or lower than the threshold value.

In another example, the weights assigned to the different intensity values may decrease or become smaller with an increasing difference between the respective intensity value and the corresponding maximum or reference value taken from the corresponding at least one mask image. This approach may take into account the possibility of low concentrations of the contrast agent being present in a part of the object corresponding to one of the remaining pixels. Using a monotonically decreasing weight function may therefore lower an impact or influence of intensity values of remaining pixels corresponding to parts of the object where some contrast agent is present. If, for example, the predetermined threshold value is set too low, the weight function may be used to mitigate a resulting effect on the image quality of the processed images.

In a development of the present embodiments, a noise-reducing filter is applied to the raw images before generating the set of processed images. The noise-reducing filter may, in other words, be used to prepare or pre-process the raw images before the at least one mask image or the at least one noise-reduced mask image is subtracted. This provides that applying the noise-reduced filter results in pre-processed or modified raw images, and the respective mask image is subtracted not from the original raw images but from the pre-processed or modified raw images. This approach may improve the image quality or clarity of the resulting processed images. If, for example, a thresholding technique is used, and the intensities of different raw images are smoothed or averaged. The resulting averaged intensity may more closely match the intensity values of the respective mask image, resulting in clearer, more easily readable processed images with less artifacts or features not corresponding to the contrast agent. It may also be possible to use a bilateral filter or a joint bilateral filter that may reduce noise while preserving detail. It may also be possible to use guided spatial smoothing to de-noise the images while keeping edges sharp and therefore preventing the raw images from becoming less sharp because of the filtering or de-noising.

In a development of the present embodiments, after the at least one mask image or the at least one noise-reduced mask image is used, a noise-reducing filter is applied to generate the set of processed images. This noise-reducing filter may be the same and/or use the same techniques as described with respect to the approach of applying a noise-reducing filter to the raw images before generating the set of processed images. The noise-reducing filter may, in other words, be applied after the respective mask image has been subtracted from the raw image as an additional image processing act to generate the processed images. This may also result in an improved image quality of the processed images. This may thus lead to easier readability and/or more accurate understanding and diagnosis.

In a development of the present embodiments, a detector used to capture the raw images or corresponding image data is moved continuously during the single contrast run to obtain the raw images. The raw images or the corresponding image data may, in other words, be acquired continuously. At the same time, there may be a relative movement or motion between the object and the detector. This provides that the detector may be moved while the imaged object remains stationary. In one embodiment, the object may be continuously moved instead of or in addition to moving the detector during the single contrast run to achieve the same result and advantages as only moving the detector. Employing a continuous relative motion between the detector and the object during the single contrast run may be implemented or realized with less effort and improved precision or control and reproducibility as compared to alternatingly moving the detector from one discrete imaging position to the next and stopping or halting the detector in between. Another advantage is that a usability of a corresponding imaging apparatus including the detector may be improved, resulting in a lowered chance for operating errors or handling errors.

In a development of the present embodiments, an absorbed dose per raw image is varied over the single contrast run in dependence of a respective number of times a respective part of the object is imaged during the single contrast run. The dose per image absorbed by the object or the dose or amount of radiation used to irradiate the object for each image may, in other words, be set in dependence of a height of the pixel stacks to which the respective image contributes. Even though the pixel stacks are only generated or created after the contrast run is complete by aligning the raw images, the height of the pixel stacks for each part of the object (e.g., the number of times each part of the object is imaged during the single contrast run) may be known in advance (e.g., before the single contrast run is started). For this purpose, the total number of raw images to be taken as well as a relative motion between the imaging device and the object as well as a timing or temporal correlation between the relative motion and the respective recording time of each raw image may be predetermined. Using this approach, it is, for example, possible to lower the dose of radiation for raw images that are completely overlapped by multiple other raw images and, therefore, picture parts of the object that are imaged multiple times during the single contrast run.

Ordinarily, using a lower dose may result in a reduced image quality. With the present embodiments, however, the image quality may be maintained despite the lowered dose by using multiple pixels of each pixel stack to reduce noise in the corresponding mask image or images and/or the respective raw image and/or the respective corresponding processed image. Specifically, at least first and last raw images taken during the single contrast run may be taken using a higher radiation dose then is used for taking a spatially and/or temporally more central raw image in a middle part of the single contrast run. Overall, this approach may result in reduced exposure of the object while maintaining image quality.

In a development of the present embodiments, a value of at least one acquisition parameter used for obtaining the raw images by the single contrast run is changed during the single contrast run. The respective raw images are then grouped corresponding to the different values of the acquisition parameter used during the single contrast run. Each group of the raw images is then processed separately. Since setting the at least one acquisition parameter to a different value may lead to corresponding differences in the raw images, grouping the raw images, and treating and processing the groups separately in dependence of the respectively used value of the at least one acquisition parameter may result in an improved, more consistent image quality of the processed images. Since this approach allows for at least maintaining the image quality, the method becomes more flexible, because the at least one acquisition parameter may be adjusted according to specific needs, a specific use case or application, and/or specific characteristics of the imaged object.

The at least one acquisition parameter may, for example, be an aperture of an optical element in a path of the radiation used to acquire or generate the raw images. This may, for example, allow for effective and efficient imaging of an irregularly shaped object with varying widths or diameter. Processing the groups of raw images separately may provide that separate pixel stacks are formed and evaluated for each different group, separate MIPs are carried out, and at least one mask image and/or at least one noise-reduced mask image is separately generated for each individual group using only the raw images of that specific group. The mask images are then only used for the corresponding group of raw images. In one embodiment, different and/or differently tuned or adjusted image processing acts are applied to the raw images of the different groups to generate the processed images. It is, for example, possible to adjust a parameter of an image processing algorithm used to generate the processed images in dependence of a value of the at least one acquisition parameter used in acquiring the respective raw image.

A boundary between two groups may correspond to a dispersal front of the contrast agent, providing that each group of raw images contains pixels corresponding to parts of the object not flooded with the contrast agent so that at least one mask image may be generated for each group.

In a development of the present embodiments, a registration algorithm is used to align the raw images. Using the registration algorithm, it may, for example, be possible to analyze the raw images to detect one or more features that are present in multiple raw images, and to then align these multiple raw images using the one or more detected features as a reference. This may be advantageous if a position of a detector used to capture the raw images is unknown in relation or with reference to a position of the object, or if the position of the detector is not known with a precision or accuracy enabling an alignment of the raw images with pixel-level accuracy by itself. Even if the detector position is known, the registration algorithm may be used supportively to improve or ensure a precise alignment of the raw images. The registration algorithm may be used very effectively to achieve the pixel-level accuracy in the alignment of the raw images in peripheral digital subtraction angiography (DSA) applications, where only a one-dimensional relative movement (e.g., a displacement or offset of different raw images in only one direction) is to be evaluated or determined.

Another aspect of the present embodiments, in addition to the described method, is an apparatus for generating a set of processed images of an object from overlapping raw images. The raw images are obtained by a single contrast run. Therein, the apparatus includes an alignment unit configured to align the raw images so that pixels representing the same part of the picture object in different raw images are aligned, forming a respective pixel stack for each pictured part of the object. The apparatus further includes a mask generation unit configured to generate at least one mask image by a maximum intensity projection through the pixel stacks of the aligned raw images. The apparatus further includes an image processing unit configured to generate the set of processed images from the raw images using the at least one mask image. The apparatus may, in other words, be configured to carry out at least one embodiment of the method. The apparatus may include a processing unit (CPU) and a data store accessible by the processing unit. The alignment unit, the mask generation unit, and/or the image processing unit may be part of the CPU.

In a development of the apparatus according to one or more of the present embodiments, the apparatus includes an image acquisition unit or imaging device and a feeding mechanism. Therein, the feeding mechanism is configured to perform or effectuate a relative motion between the object and the imaging device to execute the single contrast run. The apparatus is further configured to obtain the raw images by the imaging device. The imaging device may include a radiation source and a corresponding radiation detector. The feeding mechanism may include a drive unit as well as electrical and/or mechanical components configured to effectuate the relative motion by moving the imaging device (e.g., the detector, the object, and/or an object mount or object support).

Another aspect of the present embodiments is a storage medium containing program code configured to execute at least one embodiment of the method when the program code is executed by a processing unit (e.g., a processor). The processor may be the CPU of the apparatus according to the present embodiments. The apparatus according to the present embodiments may include the storage medium.

The embodiments and developments of the method according as well as the corresponding advantages may be applied to the apparatus according to the present embodiments, and vice versa.

Further advantages, features, and details of the present invention derive from the following description of embodiments of the present invention as well as from the drawings. The features and feature combinations previously mentioned in the description as well as the features and feature combinations mentioned in the following description of the figures and/or shown in the figures alone may be employed not only in the respectively indicated combination but also in other combinations or taken alone without leaving the scope of the invention.

In the figures, elements that provide the same function are marked with same reference signs.

DETAILED DESCRIPTION

Figure 1:
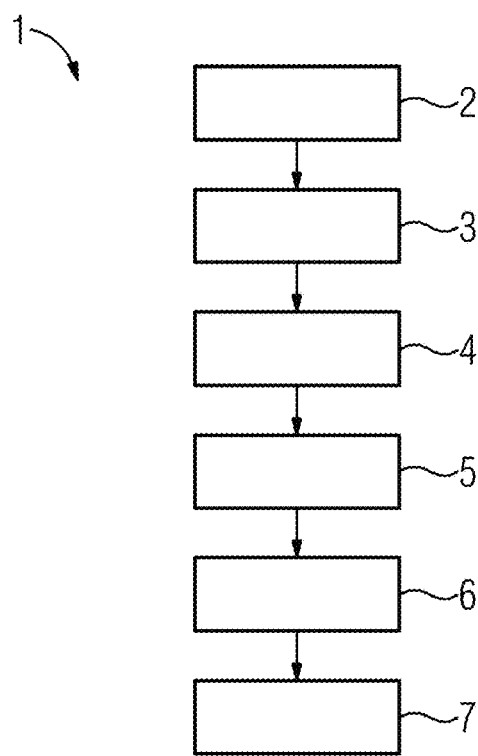
FIG. 1 schematically shows a flow chart of one embodiment of a method for generating a set of processed images.

FIG. 1 schematically shows a flowchart 1 of one embodiment of a method for generating a set of processed images. The method starts with an acquisition 2 of image data (e.g., of multiple overlapping raw images). The acquisition 2 may include accessing a data store containing the raw images. The acquisition 2 may, however, also include the actual taking or gathering of the image data by an imaging device or image acquisition device such as an x-ray apparatus. For example, a single contrast run of a peripheral angiography procedure may be executed to obtain the image data, which is then used to generate or reconstruct the multiple raw images.

The acquisition 2 is followed by an alignment act 3. In the alignment act 3, the raw images are aligned so that pixels of the raw images representing the same part of a pictured object in different raw images are aligned. Pixels of different raw images representing the same part of the object then form a respective pixel stack. For this purpose, the multiple raw images may be arranged in an image stack.

The alignment step 3 is followed by a maximum intensity projection 4 (MIP). The MIP 4 projects a highest intensity value of each of the pixel stacks on to one plane or level, thereby generating a first or initial mask image. The mask image contains the respective pixel with the maximum measured intensity value from all pixel stacks. Since the multiple raw images are taken at different points in time and may also be taken at different spatial locations, the multiple raw images picture different stages of a dispersal of a contrast agent injected into the pictured object. Building up the mask image from only the respective highest intensities for each part of the pictured object or area results in the mask image not showing the contrast agent.

The MIP 4 is followed by a process act 5, where a noise-reduced mask image is generated. In the process act 5, all pixels from the pixel stacks having intensity values lower than a predetermined threshold value are discarded, since the pixels are interpreted to correspond to object parts flooded with the contrast agent. A weighted average of the remaining pixels is then calculated for each pixel stack. These weighted average intensity values make up the noise-reduced mask image.

The process act 5 is followed by a subtraction 6 of the noise-reduced mask image from the raw images. The subtraction 6 removes image data that does not correspond to the contrast agent or parts of the object flooded with the contrast agent. The subtraction 6 therefore emphasizes the spreading or dispersing contrast agent and may make the parts of the object that are flooded with the contrast agent more clearly visible. Presently, the subtraction 6 results in a stack of intermediary processing results (e.g., intermediate images generated by subtracting the noise-reduced mask from the raw images).

In a post-processing act 7, noise in the stack of intermediate images is reduced by applying one or more image processing filters to the stack of intermediate images in a spatial and/or temporal dimension of the stack. Instead of or in addition to the post-processing act 7, such noise reducing filters may be applied to the stack of raw images prior to the subtraction 6.

These process acts from the acquisition 2 to the post-processing act 7 generate, as a result, a set of processed images with the parts of the object flooded with the contrast agent clearly visible at different stages of disposal corresponding to different points in time. The described method does not require a separate mask run to acquire a full set of mask images of the object prior to injection of the contrast agent. The described method may accommodate different image acquisition schemes or modes (e.g., where the imaging device or a corresponding detector may remain stationary, be moved stepwise between the raw images, or be moved continuously along the object). Exploitation of the fact that parts of the object are imaged multiple times during the single contrast run allows a combination of the described method with multiple different processes or methods for noise reduction.

Figure 2:
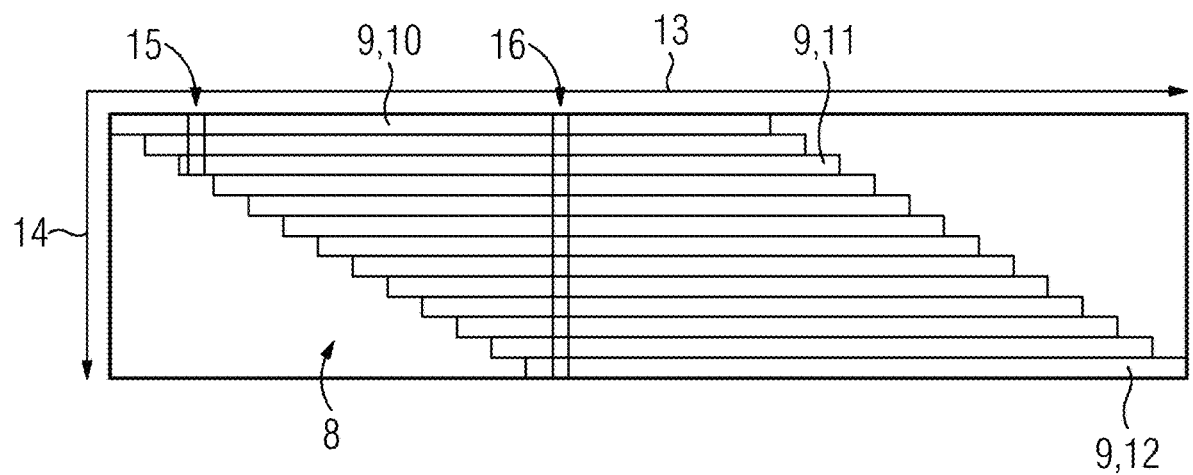
FIG. 2 schematically illustrates one embodiment of a stack of aligned raw images.

FIG. 2 schematically illustrates one embodiment of a stack 8 of aligned raw images 9. At a top of the stack 8 is a first raw image 10, and at a bottom of the stack 8 is a last raw image 12. In between the first raw image 10 and the last raw image 12 may be any number of additional raw images 9. Of these, only a third raw image 11 is specifically indicated in FIG. 2. In this case, the raw images 9 partly overlap each other giving the stack 8 a spatial structure in at least one spatial direction 13 when the raw images 9 are aligned. Since the different raw images 9 have been taken or captured at different points in time as a time series, the stack 8 also has a temporal structure as indicated by arrow 14. This provides that the first image 10 shows a different part of a pictured object at an earlier stage than the third raw image 11 as well as the last raw image 12. The raw images 9 are presently aligned so that pixels of different raw images 9 showing the same part of the object form a respective pixel stack at a specific spatial location. As an example, a first pixel stack 15 and a second pixel stack 16 are indicated. The first pixel stack 15 extends from the first raw image 10 through to the third raw image 11 and thus contains three pixels of different raw images 9. All pixels of the first pixel stack 15 show or represent the same part of the object. Due to the raw images 9 only partly overlapping, the part of the object corresponding to the first pixel stack 15 has, in this case, only been imaged three times.

The second pixel stack 16 extends all the way through the stack 8 from the first raw image 10 to the last raw image 12. The second pixel stack 16 therefore has a larger height then the first pixel stack 15, providing that the second pixel stack 16 contains more pixels. Nevertheless, all pixels of the second pixel stack 16 show or represent the same part of the object because of the alignment of the raw images 9.

Figure 3:
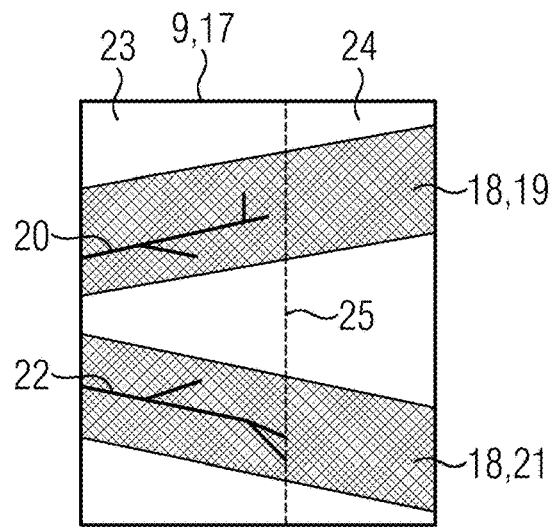
FIG. 3 schematically illustrates an example of one of the raw images from the stack shown in FIG. 2.

FIG. 3 schematically illustrates a raw image 17 that may be one of the raw images 9. Presently, the raw image 17 shows an object 18 that may, for example, be part of a patient. In this case, the object 18 is made up of a part of a left leg 19 containing a first vascular system 20, and a part of a right leg 21 containing a second vascular system 22. The raw image 17 is divided into a contrasted image part 23 and a non-contrasted image part 24 along a line 25. In this case, a contrast agent injected into the object 18 and dispersing through the vascular systems 20, 22 has reached the line 25 only in the second vascular system 22. As soon as the dispersing contrast agent-front reaches the line 25 in one and/or both of the legs 19, 21, an imaging device used to take the raw images 9 including the raw image 17 may be moved into a next position in the spatial direction 13, where a next one of the raw images 9 may then be taken.

Figure 4:
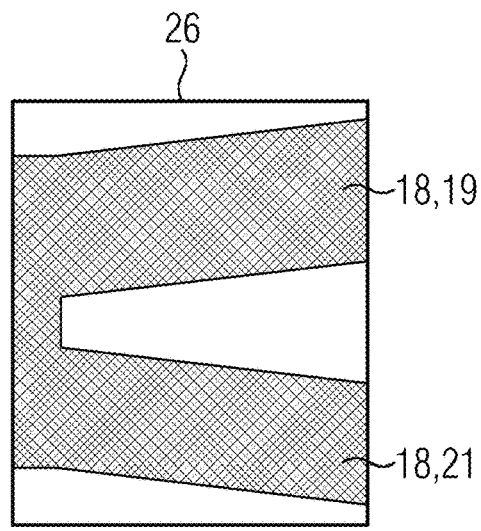
FIG. 4 schematically illustrates an example of a mask image generated from the stack of raw images shown in FIG. 2.

After all raw images 9 of the stack 8 have been taken or acquired, the MIP 4 through the stack 8 along the pixel stacks 15, 16 (e.g., along the temporal dimension indicated by arrow 14) is performed to generate a mask image 26 that is schematically illustrated in FIG. 4. Since a spatial extent of the stack 8 in the spatial direction 13 is larger than a respective extent of each individual raw image 9 in the spatial direction 13, the mask image 26 may have a larger extent in the spatial direction 13 then each of the individual raw images 9. Specifically, the extent of the mask image 26 in the special direction 13 may be equal to the extent of the stack 8 in the same special direction. The mask image 26 also shows the object 18. The mask 26 does not, however, show the contrast agent flooding the vascular systems 20, 22. For the mask image 26 to be generated without the contrast agent being visible, it is a prerequisite that during the single contrast run, every part of the object 18 pictured in the mask image 26 is imaged at least once without contrast agent being present in the respective part.

Figure 5:
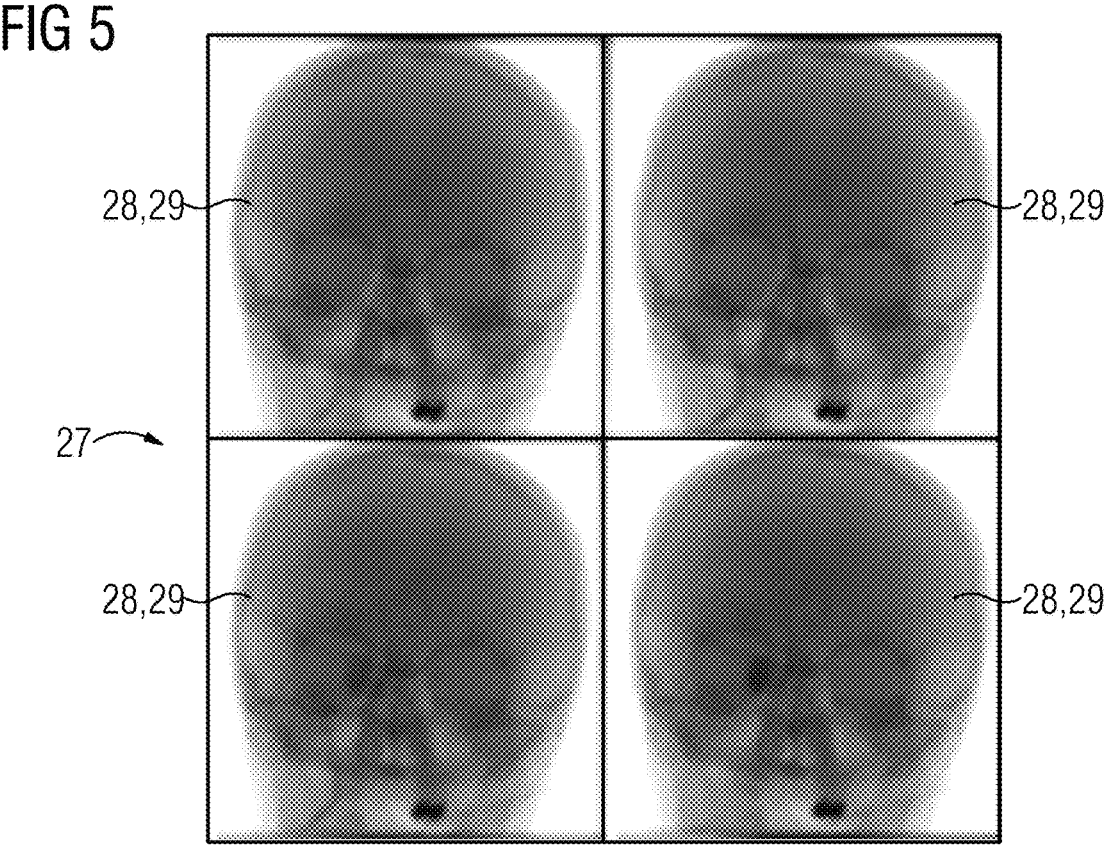
FIG. 5 schematically illustrates four exemplary raw images taken during a single contrast run.

FIG. 5 schematically illustrates a set 27 of raw images 28 of a second object 29. The raw images 28 have been taken at different points in time similar to the raw images 9. In contrast to the raw images 9, however, the raw images 28 completely overlap each other, providing that the raw images 28 have been taken without spatial displacement (e.g., without a relative motion between the second object 29 and an imaging device used to take or capture the raw images 28).

Figure 6:
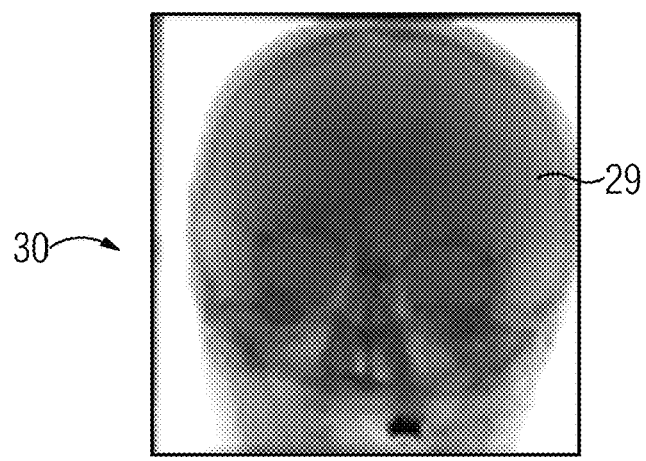
FIG. 6 schematically illustrates exemplary mask images generated from the raw images shown in FIG. 5.

FIG. 6 schematically illustrates a second mask image 30 of and for the second object 29.

Figure 7:
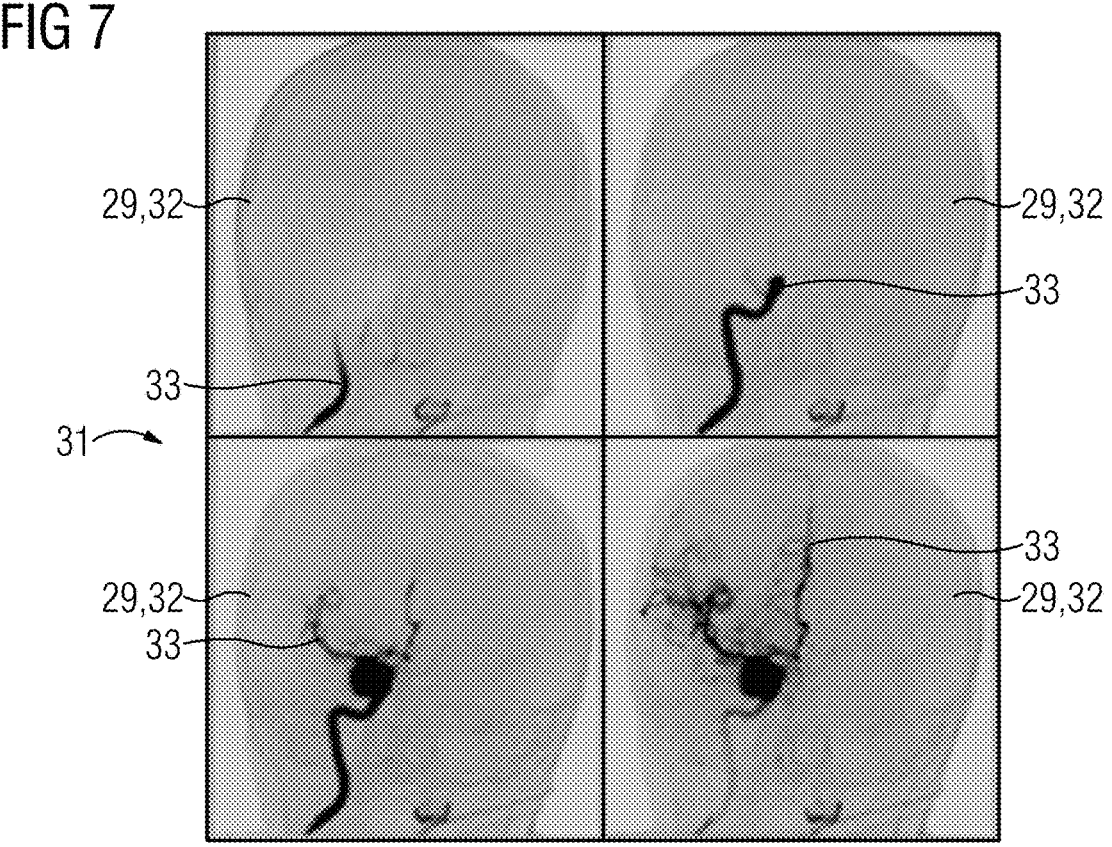
FIG. 7 schematically illustrates a set of four exemplary process images generated from the raw images shown in FIG. 5 using the mask image shown in FIG. 6.

FIG. 7 schematically illustrates a set 31 of processed images 32 of the second object 29. The processed images 32 have been generated by subtracting the second mask image 30 from the raw images 28. As compared to the raw images 28, the processed images 32 clearly show different progressive stages of dispersal of a contrast agent 33 through the second object 29.

Summing up, the examples described herein illustrate an improved method for processing raw images to generate processed images relying only on image data from a single contrast run. The method includes a mechanism for robust mask image generation.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for generating a set of processed images of an object from overlapping raw images, wherein the overlapping raw images are obtained by a single contrast run, the method comprising:
   aligning the overlapping raw images so that pixels representing a same part of the object in different raw images are aligned forming a respective pixel stack for each pictured part of the object;
   generating at least one mask image by a maximum intensity projection through the pixel stacks of the aligned overlapping raw images; and
   generating the set of processed images from the overlapping raw images using the at least one mask image.

2. The method of claim 1, further comprising:
   generating at least one noise-reduced mask image from the aligned overlapping raw images, the generating of the at least one noise-reduced mask image comprising:
      discarding all pixels from the pixel stacks having intensity values lower than a predetermined threshold value; and
      calculating a weighted average of the intensity values of the remaining pixels of each of the pixel stacks to generate the at least one noise-reduced mask image,
   wherein generating the set of processed images comprises subtracting the at least one noise-reduced mask image from each corresponding raw image of the overlapping raw images.

3. The method of claim 2, wherein the at least one mask image is used as a reference for generating the at least one noise-reduced mask image.

4. The method of claim 1, further comprising applying a noise-reducing filter to the overlapping raw images before generating the set of processed images.

5. The method of claim 1, wherein generating the set of processed images comprises applying a noise-reducing filter after the at least one mask image is used.

6. The method of claim 1, wherein a detector used to capture the overlapping raw images is moved continuously during the single contrast run to obtain the overlapping raw images.

7. The method of claim 1, wherein an absorbed dose per raw image is varied over the single contrast run in dependence of a respective number of times a respective part of the object is imaged during the single contrast run.

8. The method of claim 1, wherein a value of at least one acquisition parameter used for obtaining the overlapping raw images by the single contrast run is changed during the single contrast run,
   wherein the respective overlapping raw images are grouped corresponding to different values of the acquisition parameter, and
   wherein each group of the overlapping raw images is processed separately.

9. The method of claim 1, wherein aligning the overlapping raw images comprises aligning the overlapping raw images using a registration algorithm.

10. An apparatus for generating a set of processed images of an object from overlapping raw images, wherein the overlapping raw images are obtained by a single contrast run, and wherein the apparatus comprises:
    an alignment unit configured to align the overlapping raw images so that pixels representing a same part of the object in different raw images of the overlapping raw images are aligned forming a respective pixel stack for each pictured part of the object;
    a mask generation unit configured to generate at least one mask image by a maximum intensity projection through the pixel stacks of the aligned overlapping raw images; and
    an image processor configured to generate the set of processed images from the overlapping raw images using the at least one mask image.

11. The apparatus of claim 10, further comprising an imaging device and a feeding mechanism,
    wherein the feeding mechanism is configured to perform a relative movement between the object and the imaging device to execute the single contrast run, and
    wherein the apparatus is configured to obtain the overlapping raw images using the imaging device.

12. A non-transitory computer-readable storage medium that stores instructions executable by a processor to generate a set of processed images of an object from overlapping raw images, wherein the overlapping raw images are obtained by a single contrast run, the instructions comprising:
    aligning the overlapping raw images so that pixels representing a same part of the object in different raw images are aligned forming a respective pixel stack for each pictured part of the object;

generating at least one mask image by a maximum intensity projection through the pixel stacks of the aligned overlapping raw images; and generating the set of processed images from the overlapping raw images using the at least one mask image.

13. The non-transitory computer-readable storage medium of claim 12, wherein the instructions further comprise:

generating at least one noise-reduced mask image from the aligned overlapping raw images, the generating of the at least one noise-reduced mask image comprising:

discarding all pixels from the pixel stacks having intensity values lower than a predetermined threshold value; and calculating a weighted average of the intensity values of the remaining pixels of each of the pixel stacks to generate the at least one noise-reduced mask image, wherein generating the set of processed images comprises subtracting the at least one noise-reduced mask image from each corresponding raw image of the overlapping raw images.

14. The non-transitory computer-readable storage medium of claim 13, wherein the at least one mask image is used as a reference for generating the at least on noise-reduced mask image.

15. The non-transitory computer-readable storage medium of claim 12, wherein the instructions further comprise applying a noise-reducing filter to the overlapping raw images before generating the set of processed images.

16. The non-transitory computer-readable storage medium of claim 12, wherein generating the set of processed images comprises applying a noise-reducing filter after the at least one mask image is used.

17. The non-transitory computer-readable storage medium of claim 12, wherein a detector used to capture the overlapping raw images is moved continuously during the single contrast run to obtain the overlapping raw images.

18. The non-transitory computer-readable storage medium of claim 12, wherein an absorbed dose per raw image is varied over the single contrast run in dependence of a respective number of times a respective part of the object is imaged during the single contrast run.

* * * * *